United States Patent [19]

Löbberding et al.

[11] Patent Number: 5,169,842
[45] Date of Patent: Dec. 8, 1992

[54] OLIGOPHOSPHATES WITH AN ANTIVIRAL ACTION

[75] Inventors: Antonius Löbberding, Wuppertal; Axel C. Heitmann, Overath; Burkhard Mielke, Leverkusen; Udo Stropp, Haan; Axel Kretschmer, Bergisch Gladbach; Helga Rübsamen-Waigmann, Bad Soden; Lothar Biesert; Haryadi Suhartono, both of Frankfurt am Main, all of Fed. Rep. of Germany

[73] Assignee: Bayer Aktiengesellschaft, Leverkusen, Fed. Rep. of Germany

[21] Appl. No.: 697,870

[22] Filed: May 9, 1991

[30] Foreign Application Priority Data

May 16, 1990 [DE] Fed. Rep. of Germany ....... 4015715

[51] Int. Cl.$^5$ ............... A61K 31/675; C07F 9/02; C07F 9/06
[52] U.S. Cl. ............... 514/86; 544/243; 549/218
[58] Field of Search ............... 549/218; 544/243; 514/86

[56] References Cited

U.S. PATENT DOCUMENTS

| | | | |
|---|---|---|---|
| 4,882,321 | 11/1989 | Maurer et al. | 544/243 |
| 4,908,453 | 3/1990 | Cocuzza | 544/243 |
| 4,940,698 | 7/1990 | Mauser et al. | 544/243 |
| 5,032,680 | 7/1991 | Kawai et al. | 544/243 |
| 5,034,529 | 7/1991 | Freeman | 544/243 |
| 5,036,058 | 7/1991 | Jaeggi | 544/243 |

FOREIGN PATENT DOCUMENTS

| | | | |
|---|---|---|---|
| 279259 | 8/1988 | European Pat. Off. | 544/243 |
| 2703310 | 8/1978 | Fed. Rep. of Germany | 544/243 |
| 226892 | 9/1989 | Japan | 544/243 |

OTHER PUBLICATIONS

Aids Research and Human Retroviruses, vol. 5, No. 6, 1989, pp. 639–646.
Carbohydrate Research, 128 (1984), pp. C9–C10.
Tetrahedron Letters, vol. 29, No. 43, pp. 5549–5552, 1988.
The Journal of Biological Chemistry, vol. 262, Issue of Jul. 25, pp. 10171–10179, 1987.
Scientific American, Jan. 1990, pp. 40–46.
Tetrahedron Letters, vol. 22, No. 20, pp. 1859–1862, 1981.
J. Am. Chem. Soc. 1984, 106, 6076–6077.
J. Am. Chem. Soc. vol. 112, No. 3, 1990, 1252–1254.
J. Med Chem., 1987, 30, 1494–1497.
Nucleic Acids Research, vol. 15, No. 7, 1987.
Nucleic Acids Research, vol. 14, No. 13, 1986.

*Primary Examiner*—Cecilia Tsang
*Attorney, Agent, or Firm*—Sprung, Horn, Kramer & Woods

[57] ABSTRACT

Novel oligophosphates with an antiviral action of the formula

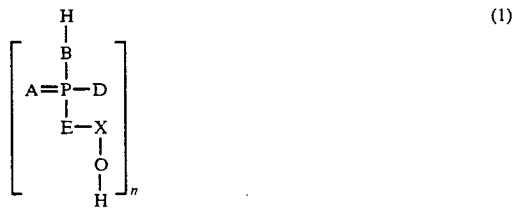

in which
n is 3–50,
B and E are, independently of one another, O, S or NH,
A is O, NR or S,
D is O, S or NR$_2$, in which independently each R is H, alkyl, aralkyl or aryl, and X is —(CH$_2$)$_m$—,

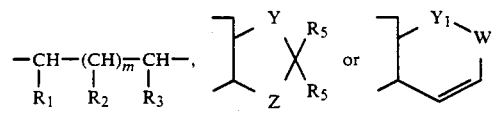

9 Claims, No Drawings

OLIGOPHOSPHATES WITH AN ANTIVIRAL ACTION

The deliberate switching off of unwanted gene expression by complementary nucleic acids, called antisense oligonucleotides, is an effective instrument for, for example, eliminating disorders with a genetic cause. This also includes the switching off of foreign nucleic acids, for example after infection by viruses, bacteria or fungi. The antisense technique entails antisense oligonucleotide derivatives hybridizing with the mRNA which is to be inhibited, so that protein synthesis based on this mRNA is suppressed. There is evidence of the action of antisense oligonucleotides in the literature.

An antiviral action has also been found with homo-oligonucleotide phosphorothioates and with oligonucleotide phosphorothioates with random sequences (Stein, C. A. et al., Aids Research and Human Retroviruses 5, 639 (1989)).

In the present invention, surprisingly, non-nucleoside oligophosphates have also been found to have antiviral properties. The latter are constructed from greatly simplified, low-cost building blocks.

The oligophosphates according to the invention have a greatly simplified chemical structure by comparison with known oligonucleotide phosphorothioates:

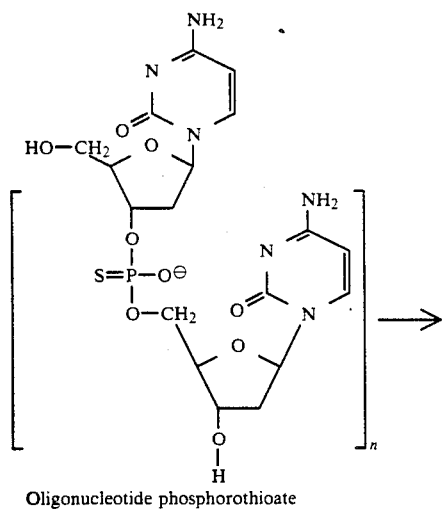
Oligonucleotide phosphorothioate

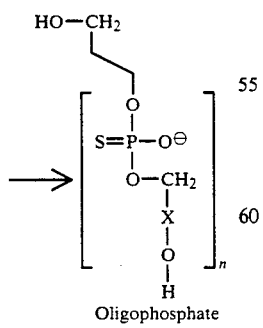
Oligophosphate where X and n have the meanings specified below.

The present invention relates to the acyclic oligophosphates of the formula (I)

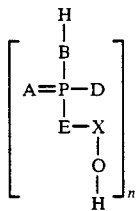

in which
n is 3-50,
B and E are, independently of one another, O, S or NH,
A is O, NR or S,
D is O, S or $NR_2$,
  in which independently each
  R is H, alkyl, preferably $CH_3$, $CH_2CH_3$ or $CH(CH_3)_2$, or aralkyl or aryl, preferably benzyl or phenyl,
and
X either denotes —$(CH_2)_m$— in which m is 1 to 5, or X denotes 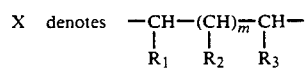

in which $R_1$, $R_2$ and $R_3$, each independently of one another, is H, —$CH_3$, —$CH_2CH_3$, —$CH(CH_3)_2$, phenyl, benzyl or —$CH_2OCH_3$, or
$R_2$ can also be F or Cl, and
m is 0 to 5,
or X denotes 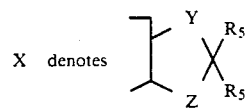

in which each
$R_5$ represents, independently of one another, H, $CH_3$, $CH_2CH_3$, $CH(CH_3)_2$, benzyl, phenyl, —$CH_2OCH_3$, O-aryl, O-alkyl, NH-aryl or NH-alkyl, O-aralkyl, NH-aralkyl
Y is NH, O, S or $CH_2$, and
Z is —$(CHR_6)_p$,
  where p is 0 to 3, and
  $R_6$ has the same meanings as $R_5$,
or X denotes 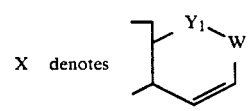

in which
$Y_1$ is NR, O, S or $CR_2$,
W is —$(CH—R_7)_i$—
  where i is zero or one, and
  $R_7$ is H, OH, alkyl, preferably $CH_3$, $CH_2CH_3$, $CH(CH_3)_2$ or aralkyl or aryl, preferably benzyl, methoxyphenyl or O-alkyl, preferably O—$CH_3$, O—$CH_2CH_3$ or O—$CH(CH_3)_2$, or O-aralkyl or O-aryl, preferably O-benzyl or O-phenyl, or NH-alkyl, preferably NH—$CH_3$, NH—$CH_2CH_3$ or NH—CH(CH3)2, or NH-aryl, preferably NH-phenyl.

(1988); M. Bobek, J. Kavai, E. De Clercq, J. Med. Chem. 30, 1494 (1987)).

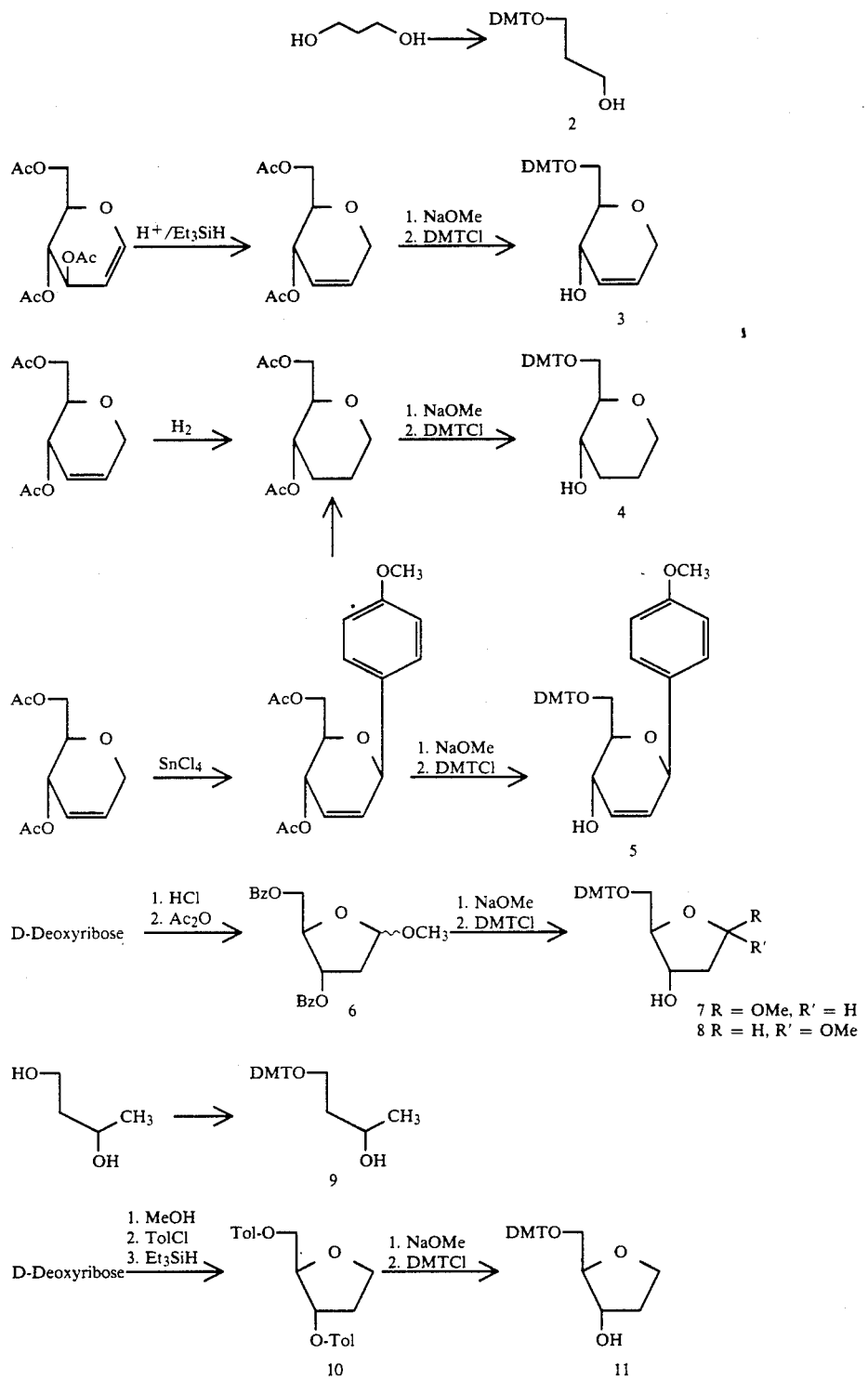

n is preferably 10 to 30 and particularly preferably 18 to 28.

The oligophosphate building blocks were prepared by known processes as may be demonstrated by the example of compounds 2, 3, 4, 5, 7, 8, 9 and 11 (G. Grynkiewicz, Carbohydr. Res. 128, C9 (1984); G. Casiraghi, M. Cornia, L. Colombo, G. Rassu, G. G. Fava, M. F. Belichi, L. Zetta, Tetrahedron Lett. 29, 5549

The dimethoxytritylation is carried out in pyridine with dimethoxytrityl chloride by known processes (F. Seela, K. Kaiser, Nucl. Acids Res. 15, 3113 (1987)).

The α/β-anomeric mixture in the case of 6 is separated by chromatography after the tritylation.

The introduction of the 1-deoxy functionality into 10 takes place by reduction with triethylsilane (M. Takeshita, C. -N. Chang, F. Johnson, S. Will, A. P. Grollman, J. Biol. Chem. 262 (1987), 10 171).

Linkage of the oligophosphate building blocks

The oligophosphates are synthesized preferably by solid-phase synthesis but also in liquid systems. For this purpose, the precursors 2, 3, 4, 5, 7, 8, 9 and 11 were converted by a known process into the hydrogen phosphates (B. C. Froehler, P. G. Ng, M. D. Matteucci, Nucl. Acids Res. 14, 5399 (1986)) 12, 13, 14, 15, 16, 17, 18 and 19 or phosphoramidates (S. L. Beaucage, M. H. Caruthers, Tetrahedron Lett. 22, 1859 (1981)) and linked together. The subsequent oxidation is likewise carried out by a known process (W. J. Stec et al., J. Am. Chem. Soc. 106, 6077 (1984) or P. I. Radhakrishnan et al. J. Am. Chem. Soc. 112, 1253 (1990)). Oligophosphates with chain lengths from 10 to 50 have been synthesized.

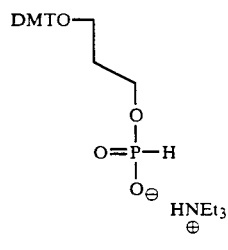
12

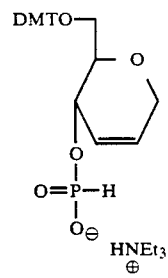
13

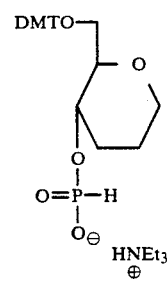
14

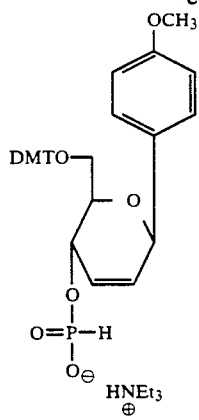
15

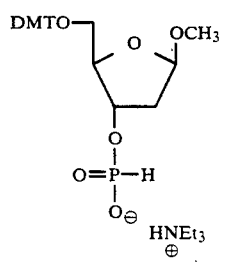
16

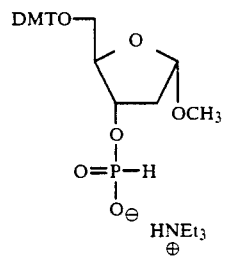
17

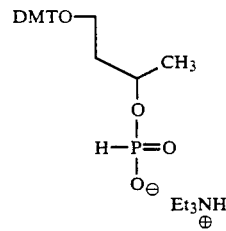
18

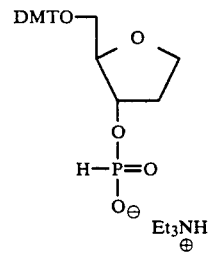
19

SYNTHESIS EXAMPLES

Example 1

1-(4.4'-dimethoxytriphenylmethoxy)-3-propanol 1.3-propanediol (5.5 g; 72.4 mmol) was added to a solution of (4.4'-dimethoxytrityl)chloride (4.9 g; 14.5 mmol) and diisopropylamine (5.0 ml; 28.7 mmol) in dry pyridine (60 ml). This solution was kept at r.t. for 6 h, then diluted with dichloromethane (200 ml), washed with sat. NaHCO₃ solution and water. The organic layer was dried (MgSO₄) and evaporated. The crude product was purified by chromatography on silica gel (eluant: dichloromethane incl. 1% Triethylamine).

Yield: 4.57 g (83%).

Example 2

4.6-di-O-acetyl-1.5-anhydro-2.3-dideoxy-D-erythro-hex-2-enitol 3,4,6-tri-O-acetyl-D-glucal (9.70 g; 35.6 mmol) was reacted at 0° C. with triethylsilane (4.96 g; 42.7 mmol) and borontrifluoride-etherate (3.04 g; 21.4 mmol) in dichloromethane (110 ml) under an atmosphere of argon for 5 minutes. The solution was poured into aqueous NaHCO₃ solution and extracted several times with dichloromethane. The organic layer was dried (MgSO₄), evaporated and the crude product purified by distillation.

Yield: 5.87 g (77%).

Example 3

1.5-anhydro-2,3-dideoxy-D-erythro-hex-2-enitol 4,6-di-O-acetyl-1,5-anhydro-2,3-dideoxy-D-erythro-hex-2-enitol (16 g; 74.7 mmol) was deacetylated with 1N sodiummethoxide (5 ml) in dry methanol (50 ml) for 3,5 h at r.t. The mixture was neutralised with ion exchange resin [Lewatit CNP-LF(H⁺)] and evaporated.

Yield: 8.6 g (89%).

Example 4

1,5-anhydro-2,3-dideoxy-6-O-(4,4'-dimethoxytrityl)-D erythro-hex-2-enitol 1,5-anhydro-2,3-dideoxy-D-erythro-hex-2-enitol (0.5 g; 3.8 mmol) was reacted with (4,4'-dimethoxy-triphenylmethylmethyl)chloride (1.6 g; 4.6 mmol) and diisopropylamine (0.8 ml; 5.7 mmol) in pyridine (10 ml). The work-up procedure was the same as in example No. 1. Chromatography was performed on silica gel with toluene/ethanol (30:1, 1% triethylamine) as eluant.

Yield: 0.69 g (42%).

Example 5

4,6-di-O-acetyl-1,5-anhydro-2,3-dideoxy-D-erythro-hexitol 4,6-di-O-acetyl-1,5-anhydro-2,3-dideoxy-D-erythro-hex-2-enitol (5.17 g; 24.1 mmol) was hydrogenated on platinum/charcoal (10%) in dry methanol (20 ml) for 25 h. Filtration and evaporation yields 4.75 g of product (91%).

Example 6

1,5-anhydro-2,3-dideoxy-D-erythro-hexitol 4.6-di-O-acetyl-1,5-anhydro-2.3-dideoxy-D-erythro-hexitol (4.75 g; 22.0 mmol) was deacylated as described in example No. 3.

Yield: 2,8 g (97%).

Example 7

1,5-anhydro-2,3-dideoxy-6-O-(4,4'-dimethoxytrityl)-D-erythro-hexitol 1,5-anhydro-2,3-dideoxy-D-erythro-hexitol (3,0 g; 22,4 mmol) was reacted with dimethoxytritylchloride (9,44 g; 27,9 mmol) as described in example 4. Purification was achieved by chromatography on silica gel (eluant: toluene/ethanol 20:1, 5% triethylamine).

Yield: 4.71 g (50%).

Example 8

Methyl-2-deoxy-5-O-(4,4'-dimethoxytrityl)-α-D-ribofuranoside and methyl-2-deoxy-5-O-(4,4'-dimethoxytrityl)-β-D-ribofuranoside To a solution of methyl-2-deoxy-α/β-D-ribofuranoside (3.0 g; 20 mmol) in dry pyridine (50 ml) were added N,N-dimethyl-aminopyridine (50 mg; 0.4 mmol) and (4,4'-dimethoxytriphenylmethyl)chloride (8.3 g; 24 mmol). The solution was stirred at r.t. for 1.5 h and then diluted with diethylether (500 ml), three times washed with water (3×200 ml), dried (MgSO₄), evaporated in vacuo and several times co-evaporated with toluene. Separation of the anomeres could be achieved by chromatography on silica gel (eluant: petroleum ether/ethylacetate 6:1→1:1, 1% triethylamin).

Yield: 3.3 g (39%) α-product, 2.1 g (25%) β-product.

Example 9

(±)-1-(4,4'-dimethoxytrityloxy)-3-butanol (±)-1,3-butanediol (1.04 g; 11.5 mmol) was reacted with (4,4'-dimethoxytriphenylmethyl)chloride (3.76 g; 11.1 mmol) as described in example 8.

Yield; 3.57 g (79%).

Example 10

1,2-dideoxy-3,5-di-O-(p-toluyl)-D-ribofuranose

To a solution of methyl-2-deoxy-3,5-di-O-(p-toluyl)-α/β-D-ribofuranoside (5.0 g; 13 mmol) in dry dichloromethane (100 ml) under an atmosphere of argon were added subsequently at 0° C. triethylsilane (4.0 ml; 26 mmol) and borontrifluoride etherate (3.5 ml; 26 mmol). The solution was stirred at 0° C. for 1 h and at r.t. for 1 h. Thereafter NaHCO₃-solution (200 ml) was added and further 10 minutes stirred at r.t. The mixture was diluted with dichloromethane (250 ml) and water (250 ml) was added. The organic layer was separated, the water layer twice extracted with dichloromethane. The combined organic layers were dried (MgSO₄) and evaporated. The resulting residue was chromatographed on silica gel with n-hexane/ethylacetate 10:1 as eluant.

Yield: 3.7 g (80%).

Example 11

1,2-dideoxy-D-ribofuranose 1,2-dideoxy-3,5-di-O-(p-toluyl)-D-ribofuranose (25.0 g; 68 mmol) was deacetylated with 1N sodium methoxide as described in example 3. The crude material was purified by chromatography on silica gel with dichloromethan/methanol (30:1→10:1).

Yield: 7.4 g (92%).

Example 12

1,2-dideoxy-5-O-(4,4'-dimethoxytrityl)-D-ribofuranose 1,2-dideoxy-D-ribofuranose (1.7 g; 14.4 mmol) was dimethoxytritylated as described in example 8. Purification of the crude product was performed by chromatography on silica gel (toluene/ethylacetate 9:1→5:1, 1% triethylamine).

Yield: 5.4 g (89%).

Example 13 triethylammonium-[methyl-2-deoxy-5-O-(4,4'-dimethoxytrityl)-β-D-ribofuranoside-3-O-hydrogenphosphonate]

1,2,4-triazole (5.3 g; 76.7 mmol) was dissolved in dry dichloromethane (220 ml) under an atmosphere of argon. N-methylmorpholine (25.6 ml) was added and the solution cooled to 0° C. Subsequently Phosphorustrichloride (2.1 ml; 24 mmol) was added, 30 minutes stirred at r.t., again cooled to 0° C. and a solution of methyl-2-deoxy-5-O-(4,4'-dimethoxytrityl)-β-D-ribofuranoside (2.1 g; 4.7 mmol) in dichloromethane (70 ml) added dropwise over a period of 60 minutes. After 90 minutes at r.t. the reaction mixture was poured into saturated triethylammoniumhydrogencarbonate solution (900 ml). The organic layer was separated, extracted twice with water, dried (MgSO4) and evaporated. The crude product was chromatographed on silica gel (eluant: toluene/ethanol 1:1, 1% triethylamine).

Yield: 2.1 g (73%).

Example 14 triethylammonium-[methyl-2-deoxy-5-O-(4,4'-dimethoxytrityl)-α-D-ribofuranoside-3-O-hydrogenphosphonate]

methyl-2-deoxy-5-O-(4,4'-dimethoxytrityl)-α-D-ribofuranoside (3.3 g; 7.3 mmol) was transformed to the hydrogenphosphonate as described in example 13.

Yield: 3.2 g (71%).

Example 15 triethylammonium-[1,2-dideoxy-5-O-(4,4'-dimethoxytrityl)-D-ribofuranose-3-O-hydrogenphosphonate]

1,2-dideoxy-5-O-(4,4'-dimethoxytrityl)-D-ribofuranose (2.0 g; 4.8 mmol) was transformed to the hydrogenphosphonate as described in example 13.

Yield: 2.4 g (85%).

Example 16 triethylammonium-[(±)-1-(4,4'-dimethoxytrityloxy-3-butanol]-3-O-hydrogenphosphonate (±)-1-(4,4'-dimethoxytrityloxy)-3-butanol (3.5 g, 6.3 mmol) was reacted as described in example 13.

Yield: 3.3 g (94%).

Example 17 triethylammonium-[1-(4,4'-dimethoxytrityloxy)-3-O-propanol]-3-O-hydrogenphosphonate 1-(4,4'-dimethoxytrityloxy)-3-propanol (3.8 g; 10.0 mmol) was reacted according to the procedure described in example 13.

Yield: 4.5 g (82%).

Example 18 triethylammonium-[1,5-anhydro-2,3-dideoxy-6-O-(4,4'-dimethoxytrityl)-D-erythro-hexitol]-4-O-hydrogenphosphonate 1,5-anhydro-2,3-dideoxy-6-O-(4,4'-dimethoxytrityl)-D-erythro-hexitol (6.35 g; 15.1 mmol) was reacted as described in example 13.

Yield: 7.63 g (84%).

Example 19

Procedure for the synthesis of oligophosphate of formula

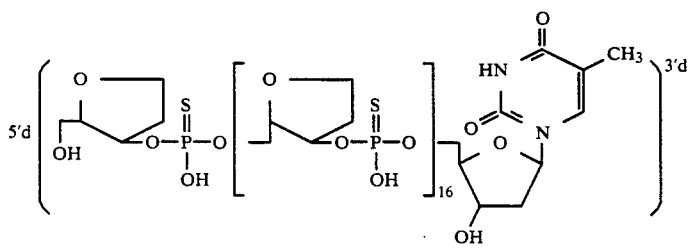

(General Procedure)

The synthesis of the oligophosphate was performed on an Applied Biosystems 380B DNA-synthesizer starting with a commercial (Applied Biosystems) control pore glass 10 μmol thymidine column. The 4,4'-dimethoxytrityl (DMT) protective group is cleaved from the 5'-hydroxy function of thymidine by treatment with 2,5 percent dichloroacetic acid in $CH_2Cl_2$. Excess dichloroacetic acid is washed out with acetonitrile. A 0.5 m solution of triethylammonium [1,2-dideoxy-5-O-(4,4'-dimethoxytrityl)-D-ribofuranose-3-O-hydrogenphosphonate] monomer in dry acetonitrile/pyridine (1:1) is activated with a 0.5 m solution of 1-adamantane-carbonyl chloride in acetonitrile/pyridine (1:1) for 80 sec and then given to the reaction column.

Excess reagent is separated by washing with acetonitrile/pyridine (1:1) after 120 sec. The capping procedure was performed according the Applied Biosystems user bulletin issue No. 44 (1987) by delivering of an equimolar mixture of isopropylphosphite and 1-adamantane-carbonyl chloride to the column. Excess reagent is washed out with acetonitrile.

The next coupling cycle started again with the cleavage of the 4,4-dimethoxytrityl group by treatment with 2.5 percent dichloroacetic acid and so on. Accordingly the synthetic cycle is repeated 16 times.

The sulfuration is performed off the DNA-synthesizer by treatment of the hydrogenphosphonate intermediate with a 0,2M solution of $S_8$ in carbon disulfide/pyridine 1:1 for one hour. Excess reagent is separated by washing with carbon disulfide/pyridine.

The oligophosphate is removed form the polymer by treatment with concentrated ammonia for 1 h. Then the product is purified by HPLC chromatography on a RP 18 column, using a linear gradient of increasing acetonitrile concentration over 30 minutes in 0.1M triethylammonium acetate.

The DMT protective group is cleaved by treatment with 80% acetic acid at room temperature for 30 minutes. The oligophosphate is isolated again by HPLC on a RP 18 column as described before.

Antiviral activity of oligophosphates

Oligophosphates are active against retroviruses, especially against the HIV virus.

The oligophosphates were tested on the virus isolates listed hereinafter:

HIV-1$_{K31,Zaire}$  isolated by Dr. von Briesen and Prof. H. Rübsamen-Waigmann, Georg-Speyer-Haus, Frankfurt 1987

HIV-2$_{ROD}$  isolated by Pasteur Institute Paris 1986.

The test system used was umbilical lymphocytes from neonates, which had been preactivated with phytohaemagglutinin. The substances were added to the cell culture immediately after the infection. The following table lists the concentrations at which syncytia formation was no longer detected.

| Compound | Building block | HIV 1 µg/ml | µmol | HIV 2 µg/ml | µmol |
|---|---|---|---|---|---|
| | | enriched CD4 lymphocytes | | | |
| 20 | 12 | 5–10 | 2–4 | 5–10 | 2–4 |
| 21 | 13 | 5–10 | 1.6–3.2 | 5–10 | 1.6–3.2 |
| 22 | 14 | — | — | 5–10 | 1.5–0.3 |
| 23 | 19 | — | — | 0.75 | 0.2 |

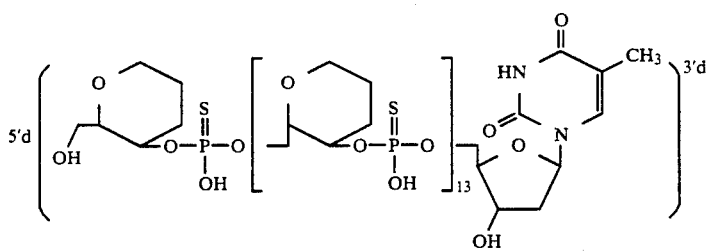

22

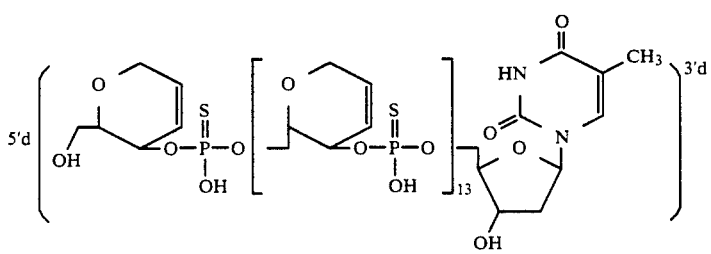

21

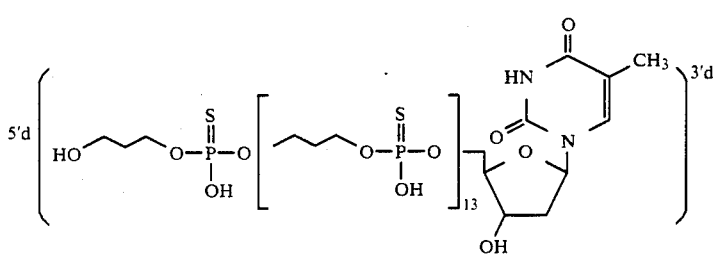

20

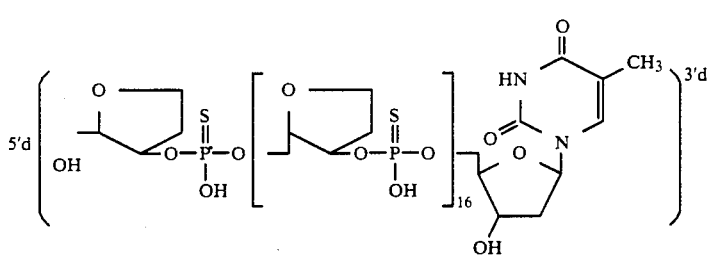

23

The corresponding pharmaceutical preparations contain besides the oligophosphates the auxiliaries customary for parenteral preparations such as, for example, buffers and/or stabilizers or liposome formulations. Topical administration is also conceivable. Examples of the preparations which can be employed for this are ointments, creams, solutions or plasters, which, besides the active compound, contain the pharmaceutical auxiliaries suitable for this administration.

It will be understood that the specification and examples are illustrative but not limitative of the present invention and that other embodiments within the spirit and scope of the invention will suggest themselves to those skilled in the art.

We claim:

1. An acyclic oligophosphate of the formula

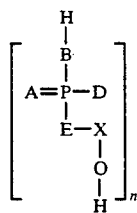

in which
n is 3-50,
B and E are O,
A is O or S,
D is O, S or NR₂ if A=O
  in which independently each
  R is H, alkyl, aralkyl or aryl,
and
X either denotes —(CH₂)ₘ— in which m represents 1 to 5,
or

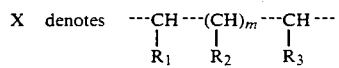

in which R₁, R₂ and R₃, each independently of one another, is H, —CH₃, —CH₂CH₃, —CH(CH₃)₂, phenyl, benzyl or —CH₂OCH₃, or R₂ can also be F or Cl, and m is 0 to 5, (1)

X denotes 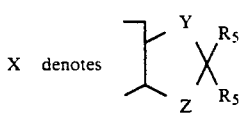

in which each
  R₅ represents, independently of one another, H, CH₃, CH₂CH₃, CH(CH₃)₂, benzyl, phenyl, —CH₂OCH₃, O-aryl, O-alkyl, NH-aryl or NH-alkyl, and
Y is O, S or CH₂, and
Z is —(CHR₆)p, where p is 0 to 3, and R₆ can have the same meanings as R₅,
or X denotes 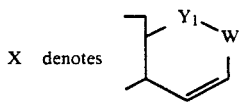

in which
Y₁ is O, S or CH₂,
W is —(CH—R₇)ᵢ—
  where i is zero or one, and
R₇ is H, OH, alkyl, aryl, O-alkyl, O-aryl, NH-alkyl or NH-aryl.

2. An acrylic oligohosphate according to claim 1, in which n is 10 to 30.

3. An acrylic oligophosphate according to claim 1, in which n is 18 to 28.

4. An acrylic oligophosphate of the formula

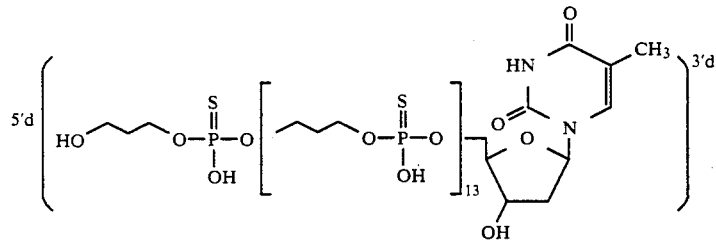

5. An acrylic oligophosphate of the formula

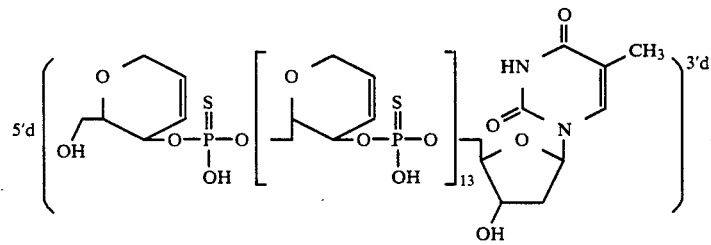

6. An acrylic oligophosphate of the formula

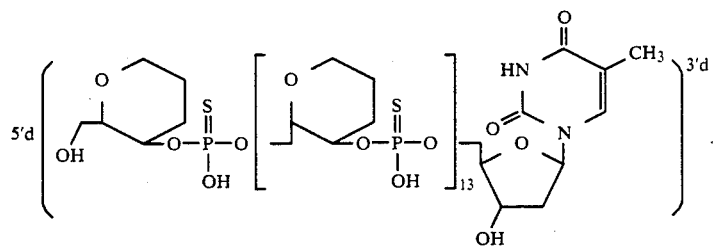

7. An acrylic oligophosphate of the formula

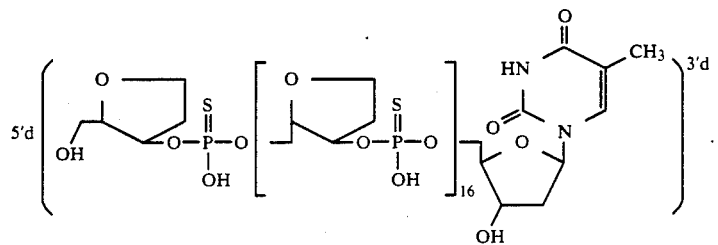

8. A composition having antiviral action against HIV 1 and HIV 2 viruses comprising an antivirally effective amount of an oligophosphate and a pharmaceutically acceptable diluent wherein the oligophosphate wherein the oligophosphate is

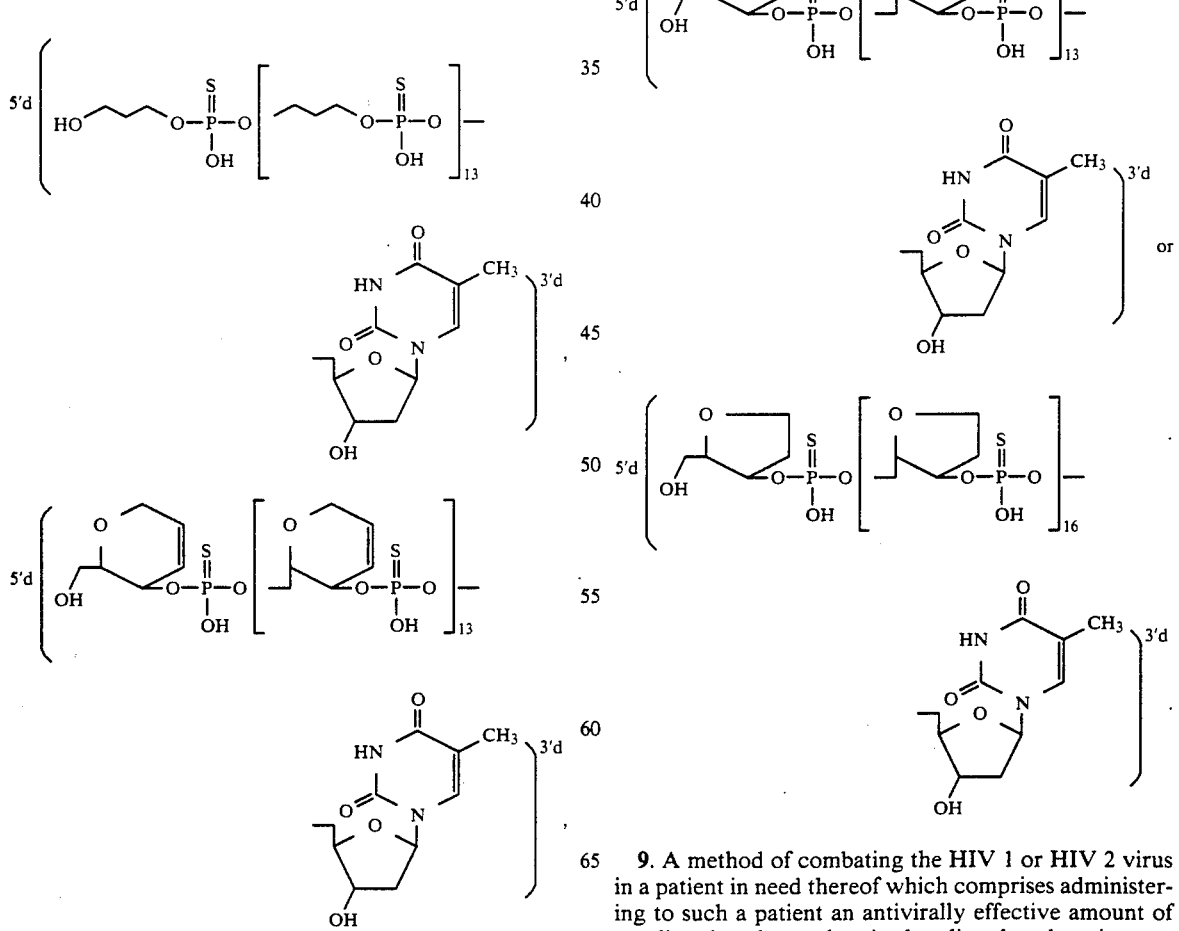

9. A method of combating the HIV 1 or HIV 2 virus in a patient in need thereof which comprises administering to such a patient an antivirally effective amount of an oligophosphate wherein the oligophosphate is

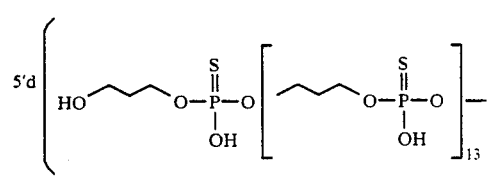
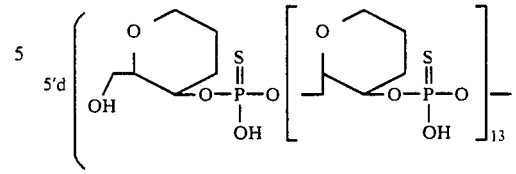
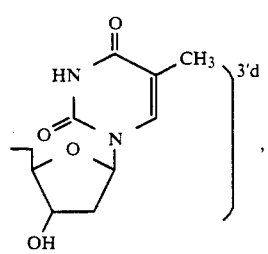
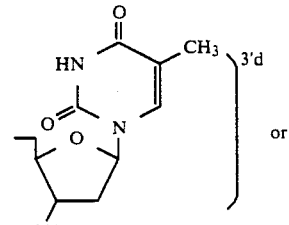
-continued
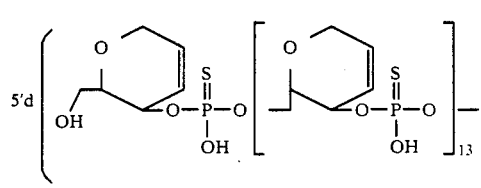
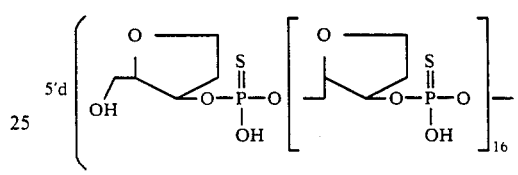
or
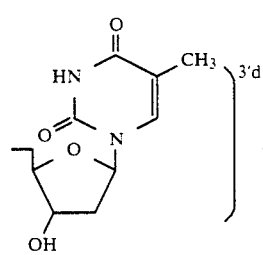
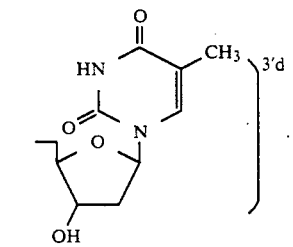
* * * * *

UNITED STATES PATENT AND TRADEMARK OFFICE
CERTIFICATE OF CORRECTION

PATENT NO. : 5,169,842
DATED : December 8, 1992
INVENTOR(S) : Lobberding, et al.

It is certified that error appears in the above-identified patent and that said Letters Patent is hereby corrected as shown below:

Col. 13, line 30   After " 0 to 5, " insert -- or --

Signed and Sealed this

Twenty-second Day of March, 1994

Attest:

BRUCE LEHMAN

*Attesting Officer*   *Commissioner of Patents and Trademarks*